US010561697B2

(12) United States Patent
Bisti et al.

(10) Patent No.: US 10,561,697 B2
(45) Date of Patent: *Feb. 18, 2020

(54) COMPOSITIONS BASED ON SAFFRON FOR THE PREVENTION AND/OR TREATMENT OF DEGENERATIVE EYE DISORDERS

(71) Applicant: Hortus Novus SRL, L'Aquila (AQ) (IT)

(72) Inventors: Silvia Bisti, Genoa (IT); Rita Maccarone, L'Aquila (IT); Maria Anna Maggi, Avezzano (IT)

(73) Assignee: HORTUS NOVUS SRL, Canistro (AQ) (IT)

( * ) Notice: Subject to any disclaimer, the term of this patent is extended or adjusted under 35 U.S.C. 154(b) by 126 days.

This patent is subject to a terminal disclaimer.

(21) Appl. No.: 15/129,019

(22) PCT Filed: Mar. 20, 2015

(86) PCT No.: PCT/IB2015/052053
§ 371 (c)(1),
(2) Date: Sep. 26, 2016

(87) PCT Pub. No.: WO2015/145316
PCT Pub. Date: Oct. 1, 2015

(65) Prior Publication Data
US 2017/0106038 A1 Apr. 20, 2017

(30) Foreign Application Priority Data
Mar. 28, 2014 (IT) .............................. MI2014A0533

(51) Int. Cl.
A61K 36/9066 (2006.01)
A61K 36/88 (2006.01)
A61K 31/12 (2006.01)
A61K 31/7028 (2006.01)
A23L 33/105 (2016.01)

(52) U.S. Cl.
CPC ............ A61K 36/88 (2013.01); A23L 33/105 (2016.08); A61K 31/12 (2013.01); A61K 31/7028 (2013.01); A61K 36/9066 (2013.01); A23V 2002/00 (2013.01)

(58) Field of Classification Search
None
See application file for complete search history.

(56) References Cited
U.S. PATENT DOCUMENTS

2004/0076691 A1 4/2004 Haines
2014/0141082 A1* 5/2014 Gao ..................... A61K 31/05
424/474
2017/0273998 A1 9/2017 Bisti et al.

FOREIGN PATENT DOCUMENTS

| CN | 103070877 A | 5/2013 |
| ES | 2428665 A1 | 11/2013 |
| GB | 2483121 A | 2/2012 |
| WO | 2015145316 A1 | 10/2015 |

OTHER PUBLICATIONS

Alavizadeh et al. (2014) Food and Chemical Toxicology 64: 64-80. (Year: 2014).*
Carmona et al. (2005) J. Agric. Food Chem. 53, 3974-3979 (Year: 2005).*
Cossignani et al. (2014) Food Chemistry 143: 446-451. (Year: 2014).*
D'Archivio et al. (2016) Food Chemistry 212: 110-116. (Year: 2016).*
Falsini et al. (2010) Invest Ophthalmol Vis Sci. 51: 6118-6124. (Year: 2010).*
Maccarone et al. (2008) Invest Ophthalmol Vis Sci. 49: 1254-1261. (Year: 2008).*
Mandal et al. (2009) Free Radical Biology and Medicine 46: 672-679. (Year: 2009).*
Maragoni et al. (2013) Journal of Translational Medicine, 11: 228(11 pages) (Year: 2013).*
Raskin et al. (2004) Current Pharmaceutical Design, 10, 3419-3429. (Year: 2004).*
Tarantilis et al. (1995): Journal of Chromatography A, 699: 107-118. (Year: 1995).*
Xuan, B et al., "Effects of Crocin Analogs on Ocular Blood Flow and Retinal Function," Journal of Ocular Pharmacology and Therapeutics, vol. 15, No. 2, Apr. 1, 1999, pp. 143-152.
Falsini, B et al., "Influence of saffron supplementation on retinal flicker sensitivity in early age-related macular degeneration," Investigative Ophthalmology & Visual Science, vol. 51, No. 12, Dec. 2010, pp. 6118-6124.
Alavizadeh, S H et al., "Bioactivity assessment and toxicity of crocin: A comprehensive review," Food and Chemical Toxicology, vol. 64, Nov. 22, 2013, pp. 65-80.
Maccarone, R et al., Saffron Supplemental Maintains Morphology and Function after Exposure to Damaging Light in Mammalian Retina, Invest. Ophthal. Visual Sci., vol. 49, No. 3, Mar. 2008, pp. 1254-1261.
Mandal, N W A et al., "Circumin Protects Retinal Cells from Light- and Oxidant Stress-induced Cell Death," Free Radic Biol Med., vol. 46, No. 5, Mar. 1, 2009, pp. 672-679.
Vasirddy, V et al., "Recue of Photoreceptor Degeneration by Curcumin in Transgenic Rats with P23H Rhodopsin Mutation," PLoS ONE, vol. 6, No. 6, Jun. 2011, pp. 1-10.
Falsini, B et al., "Retinal Sensitivity to Flicker Modulation: Reduced by Early Age-Related Maculopathy," Invest. POphth & Vis. Sci. vol. 41, No. 6, May 2000, pp. 1498-1506.

(Continued)

Primary Examiner — Russell G Fiebig
(74) Attorney, Agent, or Firm — Fredrikson & Byron, P.A.

(57) ABSTRACT

The present invention is directed to a pharmaceutical, dietary and/or food composition comprising saffron for use in the prevention and/or treatment of degenerative eye disorders. The present invention is also directed to a combination comprising saffron and curcumin, and to a pharmaceutical, dietary and/or food composition comprising said combination for use, by oral route, in the prevention and/or treatment of degenerative eye disorders.

12 Claims, 3 Drawing Sheets

(56) References Cited

OTHER PUBLICATIONS

Natoli, R et al., "Morphological, functional and gene expression analysis of the hyperoxic mouse retina," Experimental Eye Research, 92 (2001), pp. 306-314.
PCT International Search Report and Written Opinion dated Jun. 8, 2015 for Intl. App. No. PCT/IB2015/052053, from which the instant application is based, 11pgs.
International Patent Application No. PCT/IB2015/052053, International Preliminary Report on Patentability dated Apr. 18, 2016, 7 pages.
Bisti, S. et al., "Saffron and retina: Neuroprotection and pharmacokinetics," Visual Neuroscience (2014) 31, 355-361.
Marangoni, D. et al., "Functional effect of Saffron supplementation and risk genotypes in early age-related macular degeneration: a preliminary report," Journal of Translational Medicine (2013) 11:228, 11 pages.
Caballero-Ortega et al., "HPLC quantification of major active components from 11 different saffron (*Crocus sativus* L.) sources," Food Chemistry, vol. 100, 2007, pp. 1126-1131.
Esmaeal Tamaddonfard et al., "Effects of intraperitoneal and intracerebroventricular injection of crocin on acute corneal pain in rats," Phytotherapy Research, vol. 24, No. 10, May 17, 2010, pp. 1463-1467.
Fantes, Francisco E. et al, Wound healing after excimer laser keratomileusis (photorefractive keratectomy) in monkeys, 1990, (33 pgs.).
Leung et al., "Update on current and future novel therapies for dry age-related macular degeneration," Expert Rev. Clin. Pharmacol., vol. 6, No. 5, 2013, pp. 565-579.
Maggi et al., "Geographical origin differentiation of saffron spice (*Crocus sativus* L. stigmas)—Preliminary investigation using chemical and multi-element (H, C, N) stable isotope analysis," Food Chemistry, vol. 128, 2011, pp. 543-548.
Nagaki Yasunori et al., "Effects of oral administration of Gardeniae fructus extract and intravenous injection of crocetin on lipopolysaccharide- and prostaglandin E2-induced elevation of aqueous flare in pigmented rabbits," American Journal of Chinese Medicine, vol. 31, No. 5, 2003, pp. 729-738.
PCT International Search Report and Written Opinion dated Dec. 7, 2015 for Intl. App. No. PCT/IB2015/057203, 13 pgs.
Piccardi et al., "A Longitudinal Follow-Up Study of Saffron Supplementation in Early Age-Related Macular Degeneration: Sustained Benefits to Central Retinal Function," Evidence-Based Complementary and Alternative Medicine, vol. 2012, 2012, 9 pages.
Vasireddy, Vidyullatha et al., "Rescue of Photoreceptor Degeneration by Curcumin in Transgenic Rats with P23H Rhodopsin Mutation," PLoS ONE, Jun. 2011, vol. 6, Issue 6, 10 pages.

\* cited by examiner

COMPOSITIONS BASED ON SAFFRON FOR THE PREVENTION AND/OR TREATMENT OF DEGENERATIVE EYE DISORDERS

RELATED APPLICATIONS

This application is a 35 U.S.C. 371 national stage filing from International Application No. PCT/Ib2015/052053, filed Mar. 20, 2015, which claims priority to Italian Application No. MI2014A000533, filed Mar. 28, 2014, the teachings of which are incorporated herein by reference.

The present invention is directed to a pharmaceutical, dietary and/or food composition, preferably a food supplement, comprising saffron, and use thereof in the prevention and/or treatment of degenerative eye disorders.

Another aspect of the invention is directed to a pharmaceutical, dietary and/or food composition, preferably a food supplement, comprising saffron and curcumin for use in the prevention and/or treatment of degenerative eye disorders.

STATE OF THE ART

Neurodegenerative diseases are characterized by the impoverishment of nerve cells, which die as a genetic program of self-elimination, i.e. apoptosis, is triggered.

Apoptosis is the main mechanism of neuronal cell death, and of induced and hereditary retinal degenerations, such as age-related macular degeneration (AMD), and all degenerative disorders due to genetic mutations, such as, for example, retinitis pigmentosa (RP).

AMD is the most common cause of vision loss in old age.

AMD pathogenesis seems to be the result of the interaction among genetic mutations, metabolic stress of the retinal pigment epithelium and adjacent tissues, and exogenous factors, which determines the damage or death by apoptosis of the photoreceptors.

The photoreceptors are the nerve cells that convert light into electrical signals, signals which, processed at the level of the neural networks, give rise to visual perception. Their metabolism is intense and requires great amounts of oxygen. However, with the years, the mechanism tends to jam, and the oxygen which was vital may become toxic to these cells, damaging them causing eventually their death. This is what happens in various forms of senile blindness and, due to genetic defects, also in hereditary maculopathies; such as retinitis pigmentosa and Stargardt disease.

AMD specifically affects the central macular region of the retina, where both the ganglion cells and the cones are highly concentrated.

To date, various therapeutic possibilities have been offered, but the results are still modest. Photodynamic therapy, intravitreal injections of triamcinolone or of anti-angiogenic drugs are the treatments currently available on the market.

RP is typically characterized by dystrophy of cones and rods of the retina, which leads to these photoreceptors cell death, resulting in gradual and progressive loss of vision.

Epidemiological data indicate that several factors can increase or decrease the likelihood of degeneration and/or dysfunction of the photoreceptors in AMD and RP. Many risk factors are of oxidative type, while other protection factors act as antioxidants.

A protective action is attributed to dietary supplements containing antioxidants, such as carotenoids, lutein and zeaxanthin, which are constituents of the macular pigment, whose role would be to counteract the oxygen reactive species resulting from exposure to light.

Saffron, that is the stigmas of the *Crocus sativus* plant, is known for its antioxidant/anti-inflammatory activity. Recently, it was shown that its crude extract, and purified derivatives thereof, are able to prevent tumors formation, atherosclerosis, and liver and kidney damage.

The chemistry of saffron is complex and there are many types of saffron, obtained from different varieties and differently prepared.

These varieties differ in the amount of their components, such crocins, crocetins (carotenoid derivatives), picrocrocin, campherol and safranal.

Recent experimental studies describe the role of saffron in neuroprotection of retinal photoreceptors undergoing oxidative stress (Maccarone et al. *Invest. Ophthal. Visual Sci.* 49(3):1254-61, 2008). In these experiments, it was possible to demonstrate that a saffron enriched diet maintains both the morphology and function of the photoreceptors, reducing significantly their cell death.

It was demonstrated that saffron activity in the prevention of photoreceptors apoptosis is due to crocins contained therein.

The crocins have proved capable of activating metabolic pathways to protect cells from apoptosis, and of reducing the isolated photoreceptors death caused by light. Chemically, crocins are compounds of formula I, that is diesters of the dicarboxylic acid crocetin, wherein the carboxy groups are esterified by $R_1$ and $R_2$, wherein both $R_1$ and $R_2$ groups may be, independently, gentiobiose, glucose and many other sugars:

Formula I

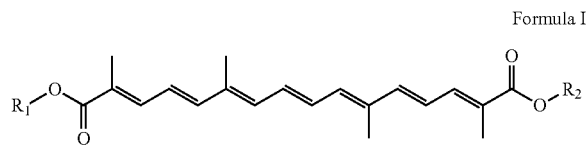

Different crocins may therefore be distinguished, in which the crocetin acid groups are esterified with different saccharides.

In the different varieties of saffron, the more abundant crocins are trans-crocin T1 (trans-crocin-4-gentiobiose-gentiobiose), of formula II Formula II

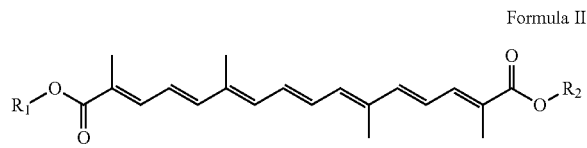

wherein $R_1=R_2=$gentiobiose, and trans-crocin T2 (trans-crocin-3-gentiobiose-glucose), of formula III Formula III

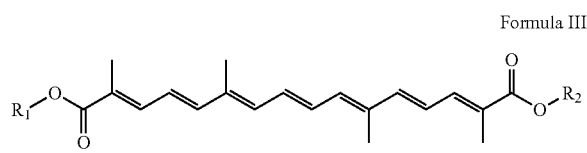

$R_1=$gentiobiose and $R_2=$glucose.

Also belong to the group of crocins analogues which have a different configuration of the 5-6 double bond of crocetin alkyl chain, i.e. compounds that have the cis configuration instead of the trans configuration, so called cis-crocins.

As mentioned above, not all varieties of saffron were equally effective in the prevention of photoreceptors apoptosis.

Moreover, the investigations carried out on varieties of saffron of different geographical origin have revealed that these different varieties of saffron mainly differ in their contents of trans and cis crocins, and also showed that the experimental results, in terms of effectiveness against cell apoptosis, vary correspondingly.

Furthermore, always in relation to the comparison of varieties of saffron of different origin, it was observed that for some of the varieties the content of different trans and/or cis crocins are not substantially constant from one harvest to another, but may vary to a not negligible extent.

It is therefore apparent that the simple reference to the use of a generic saffron as a preventive or therapeutic agent is not sufficient to ensure the desired result. For example, if the treatment protocol subsequently specified is conducted in parallel, on mice that have the same degree of ocular degeneration induced with an identical mechanism, with a saffron from central Italy, in particular from Abruzzo, Umbria and Tuscany, and respectively with one saffron produced in the Middle East (such as one produced in Iran) the obtained results are radically different, in meaning that, with the second saffron, in the same experimental conditions, improvements comparable to those achieved with the first type of saffron are of observed.

Moreover, similar results are obtained by using a saffron produced in New Zealand or Tasmania, so that the intervention or concurrence of different geographical and climatic conditions cannot be assumed, as those existing in central Italy and in Tasmania are mutually profoundly different.

Curcumin is the main biologically active component of *Curcuma longa*, which is a component of the botanical group of turmeric. Curcumin is obtained from the root and rhizome (the underground stem) of the plant.

The chemical formula of curcumin is $C_{21}H_{20}O_6$, it is also known as diferuloylmethane, and the structural formula is as follows:

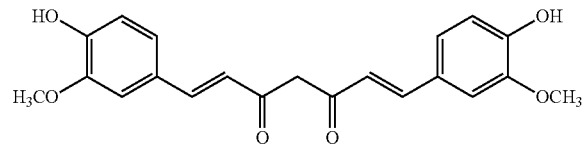 [SMILES: COc1cc(/C=C/C(=O)CC(=O)/C=C/c2ccc(O)c(OC)c2)ccc1O]

Curcumin is associated with significant anti-cancer, anti-inflammatory and antioxidant properties, and for this reason it is used as a natural treatment for a large number of diseases.

Curcumin has proven effective in the prevention of certain inflammatory and degenerative eye disorders.

For example, the administration to rats exposed to light of a diet added with 0.2% of curcumin showed a reduction in the onset of retinal oxidative and inflammatory stress, (Mandal et al. Free Radic Biol Med. 2009; 46 (5): 672-679).

Curcumin, administered in amounts of 100 mg/kg in rats affected by the P23H mutation in the rhodopsin gene, has also proved to be active in inhibiting the formation of rhodopsin aggregates. The accumulation of these aggregates is related to the photoreceptors degeneration in about 25% of autosomal forms of retinitis pigmentosa. The transgenic rats, to which curcumin was administered, showed an improvement in the morphology of the retina, and specifically in photoreceptors preservation (Vasireddy V. et al. PLoS ONE; June 2011; Volume 6 (6): 1-10).

The main object of the present invention is to provide a composition which allows curing and also preventing the degenerative eye disorders, by cure it is meant the arrest or even a partial improvement of the ocular degeneration existing at the beginning of therapy.

DESCRIPTION OF THE INVENTION

This object is achieved with a pharmaceutical, dietary and/or food composition comprising saffron in association with at least one physiologically acceptable excipient, for use in the prevention and/or treatment of degenerative eye disorders. Degenerative disorders of the eye to which the present invention is addressed are hereditary retinal degenerations, such as all degenerative forms due to genetic mutation such as retinitis pigmentosa (RP) and Stargardt disease, or induced retinal degenerations, such as age-related macular degeneration (AMD).

By "saffron" in the present invention it is meant a dried product obtained from *Crocus sativus*, comprising crocins, picrocrocin, campherol and safranal, mixture in which trans-crocin-4-gentiobiose-gentiobiose is present in an amount equal to or greater than 16.9% by weight, based on the total weight of saffron, and in which trans-crocin-3-gentiobiose-glucose is preferably present in an amount equal to or greater than 8% by weight, based on the total weight of saffron.

The present invention is therefore directed to a pharmaceutical, dietary and/or food composition, preferably a food supplement, comprising effective amounts of saffron, in which the amount of trans-crocin-4-gentiobiose-gentiobiose is equal to or greater than 16.9% by weight, based on the total weight of saffron, and the amount of trans-crocin-3-gentiobiose-glucose is preferably equal to or higher than 8% by weight, based on the total weight of the saffron, for use in the treatment of degenerative eye disorders, and particularly of degenerative forms due to genetic mutations, such as retinitis pigmentosa (RP) and Stargardt disease, or the induced retinal degenerations, such as age-related macular degeneration (AMD).

In a preferred aspect, the saffron contained in the composition of the invention originates from Abruzzo, Umbria or Tuscany regions.

The administration of the composition may occur systemically, particularly by oral route, without requiring, as in the known methods of treatment of degenerative eye disorders, the use of techniques, such as intravitreal injections or photodynamic therapy, that are highly invasive and, in any case, burdensome for the patient.

The daily dose and the duration of the treatment vary according to the indication, the age, and the patient's clinical situation.

A further specific aspect of the present invention is that the intended effect is achieved when a certain blood level of saffron is established in the patient, a level which, as established experimentally, is achieved only after 15 days of administration of an amount of saffron equal to 20 mg/day.

In other words, even if, hypothetically, the same amount of saffron corresponding to an administration of 20 mg/day was administered to a patient in a single solution, this would not achieve the blood level required for the saffron to exert its action, therefore, it seems plausible that even if the saffron is administered in excess of the aforesaid dosage, the amount in excess is expelled without any effects.

In a preferred aspect, the pharmaceutical, dietary and/or food composition of the present invention comprises effective amounts of saffron in association with at least one physiologically acceptable excipient in the same dosage unit.

Since the composition according to the present invention is realized using saffron, meant as the dried product obtained from *Crocus sativus*, the composition according to the present invention comprises an amount of *Crocus sativus* between 5 and 50 mg, being meant that the daily dose will have to comply with the limits specified above.

It was also shown that the combination of saffron with a proper amount of curcumin allows obtaining a further advantage in terms of effectiveness in the prevention and/or treatment of degenerative eye disorders.

In a further aspect, the present invention is therefore directed to a pharmaceutical, dietary and/or food composition, preferably a food supplement, comprising effective amounts of saffron, in which the amount of trans-crocin-4-gentiobiose-gentiobiose is present in quantities greater than or equal to 16.9% by weight relative to the total weight of saffron and in which trans-crocin-3-gentiobiose-glucose is preferably present in an amount equal to or greater than 8% by weight, based on the total weight of the saffron, in combination with effective amounts of curcumin, for use in the treatment of degenerative eye disorders, and particularly degenerative disorders due to genetic mutation, such as retinitis pigmentosa (RP) and Stargardt disease, or induced retinal degenerations, such as degeneration related macular (AMD).

With regard to curcumin, it was found that the effective dose is about 100 mg/day. The composition of the invention, comprising the combination of saffron and curcumin, is able to exert a greater activity than a composition comprising only saffron or curcumin alone, thus demonstrating a synergistic effect given by the combination of saffron and curcumin.

A specific feature of the present invention is the fact that the administered composition consists of substances normally classified as spices and devoid of side effects for the patient, since both saffron and turmeric (turmeric extract is the main component the so-called "curry") are usual ingredients of many recipes.

In one aspect of the present invention, the combination of saffron and curcumin is characterized in that said saffron is administered in a daily dose of 20 mg/day, and said curcumin is administered in a daily dose of 100 mg/day.

In another aspect, the present invention is directed to a pharmaceutical, dietary and/or food composition comprising saffron, in which trans-crocin-4-gentiobiose-gentiobiose is present in an amount greater than or equal to 16.9% by weight, based on the total weight of saffron, and in which trans-crocin-3-gentiobiose-glucose is preferably present in an amount equal to or greater than 8% by weight, based on the total weight of saffron and curcumin, and in association with at least one physiologically acceptable excipient, for use in the prevention and/or treatment of degenerative eye disorders, and particularly degenerative disorders due to genetic mutation, such as retinitis pigmentosa (RP) and Stargardt disease, or induced retinal degenerations, such as degeneration related macular (AMD).

The pharmaceutical, dietary and/or food compositions of the present invention are preferably formulated in solid form, said solid form being selected from tablet, granulate, dragee or capsule, more preferably tablet.

To obtain the pharmaceutical, dietary and/or food compositions according to the present invention the following classes of known excipients are preferably used: anti-caking agents, sweeteners, surfactants (cationic, anionic or non-ionic), diluents, aggregating agents or binders, lubricants, glidants, stabilizers, solubilizers, emulsifiers, humectants, flavoring agents, coating agents, colorants, acidity regulators, or a mixture thereof.

In a preferred aspect, the pharmaceutical compositions of this invention comprise saffron and curcumin in combination with at least one physiologically acceptable excipient in the same dosage unit, in the form of a tablet for oral administration. Since the composition according to the present invention is realized using saffron, meant as the dried product obtained from *Crocus sativus* and turmeric, meant as the yellow pigmented product obtained from the rhizomes of *Curcuma longa*, the composition according to the present invention comprise an amount of *Curcuma longa* ranging between 30 and 200 mg, and an amount of *Crocus sativus* ranging between 5 and 50 mg, being meant that the daily dose will have to comply with the limits specified above.

The present invention is further directed to a method for the prevention and/or treatment of degenerative disorders of the eye characterized by the administration of effective amounts of saffron, in which trans-crocin-4-gentiobiose-gentiobiose is present in an amount equal to or greater than 16.9% by weight, based on the total weight of saffron, and in which trans-crocin-3-gentiobiose-glucose is preferably present in an amount equal to or greater than 8% by weight, based on the total weight of saffron and curcumin, method which provides for the systemic daily administration of 20 mg/day of saffron and 100 mg/day of curcumin, for a time exceeding 15 days, preferably of at least three months.

In a preferred aspect, the combination and/or the pharmaceutical compositions of this invention are administered to mammals, especially to humans.

The following examples are intended to better understand the invention, without in any way limiting it.

EXAMPLES

Example 1

Morphological Analysis of the Retina

The efficacy profile associated with the administration of saffron in the activity of neuroprotection was verified by conducting a morphological analysis of the retina in SD albino rats subjected to light damage in a model of retinal degeneration, to quantify the damage and assess the possible protective activity of saffron.

In a first group, each rat was treated for 7 days with saffron dissolved in ordinary tap water, at a dose of 1 mg of saffron per Kg of body weight of the animal. The treatment was prepared daily.

A second group of rats was not subjected to any treatment.

On the seventh day the animals were subjected to a light damage for 24 h, and were subsequently treated for another 7 days. After which, they were sacrificed, the eyes explanted and the retinas isolated.

The thickness of the outer nuclear layer of the retina (ONL), which contains the photoreceptors, and the thickness of the entire retina were then measured, and the ratio of these values was calculated.

The results obtained have shown that animals pre-treated with saffron show a decreased thinning of the thickness of the retina, compared with what occurred for untreated animals.

The thickness of the retina decreases upon exposure to a light damage. The ratio between the thickness of the inner layer of the retina and the thickness of the entire retina is, therefore, indicative of the light damage suffered by the animals. The neuroprotective activity of saffron was therefore demonstrated.

Example 2

To experimentally verify the effect of the combination of saffron and curcumin according to the present invention, a composition in tablets was prepared, each tablet comprising 10 mg of *Crocus sativus* and 50 mg of *Curcuma longa* together with the usual excipients of solid compositions in which the active principles are in solid powder form.

29 patients of advanced average age (from 55 to 85 years), all suffering from bilateral macular degeneration, early and age-dependent, were divided into two groups, the first of which was subjected to administration of two tablets/day for 90 days, making a series of clinical tests at beginning of treatment and after 90 days. The investigations were concerned with the Snellen visual acuity test, the examination of the fundus through direct and indirect ophthalmoscopic investigation, and the fERG test conducted according to the technique credited (B. Falsini and others, "Retinal sensitivity to flicker modulation: reduced by early age-related maculopathy, "Investigative Ophthalmology and Visual Science, vol. 41, no. 6, pp. 1498-1506, 2000).

At the end of 90 days, after a break of 15 days, the test was repeated reversing the groups of patients (i.e. administering the placebo to the group than in the previous period had been treated with the composition of the invention).

The experiment was conducted for a total of 15 months.

The results of the experiment can be summarized as follows:

fERG Test

After three months of administration, the fERG amplitude is increased compared to the starting value, resulting in a reduction of the response threshold, as indicated by the decrease of the minimum depth of modulation, giving rise to a response significantly higher than the background level. Furthermore, the fERG data showed a modest variability in the testing and retesting sequence.

As a matter of fact, in most patients the changes in the observed response thresholds were substantially equal at the sixth and twelfth month, and such variations showed anyway a variable reduction of the threshold value compared to the corresponding starting value.

Visual Acuity Test

Already after the first three months of administration, the mean visual acuity showed an improvement of two Snellen lines and, in any case, the increase of visual acuity remained stable during the whole period of observation.

Fundus Examination

This test, periodically carried out on all patients, showed no significant changes in the number and size of drusen, as well as for what concerns the extension of the abnormalities of retinal pigment epithelium (RPE).

Finally, in parallel to the improvement of visual acuity, patients were reporting an improvement in the quality of vision, particularly for what concerns the perception of contrast and color, reading skills, and vision in low luminance, which resulted in a substantial improvement of the quality of life.

Example 3

Morphological Analysis of the Retina

The efficacy profile associated with the administration of saffron according to the present invention in the activity of neuroprotection was verified by conducting a morphological analysis of the retina in SD albino rats subjected to light damage in a model of retinal degeneration, to quantify the damage and assess the possible protective activity of saffron.

The animals were divided into four groups:

Group 1: rats treated with saffron having a content of trans-crocin-4-gentiobiose-gentiobiose (T1) greater than or equal to 16.9% and of trans-crocin-3-gentiobiose-glucose (T2) equal to or greater than 8% (saffron B);

Group 2: rats treated with saffron having a content of trans-crocin-4-gentiobiose-gentiobiose (T1) equal to 12% and of trans-crocin-3-gentiobiose-glucose (T2) equal to 6% (saffron A);

Group 3: rats untreated, but subjected to light damage (diseased retina);

Group 4: healthy animals (healthy retina).

Group 1 and 2 animals were treated for 7 days with saffron dissolved in ordinary tap water, at a dose of 1 mg of saffron per kg of animal body weight. The treatment was prepared daily.

On the seventh day the animals were subjected to a light damage for 24 hours, and were subsequently treated for another 7 days.

On the seventh day, group 3 animals were subjected to a light damage for 24 hours.

Group 4 animals were subjected neither to treatment based on saffron, nor to light damage.

On the fourteenth day all animals were sacrificed, eyes explanted and retinas isolated.

The thickness of the outer nuclear layer of the retina (ONL), which contains the photoreceptors, and the thickness of the entire retina were then measured, and the ratio of these values was calculated.

The graph in FIG. 2 shows the values of these ratios.

The results show that saffron comprising 12% of trans-crocin-4-gentiobiose-gentiobiose (T1) and 6% of trans-crocin-3-gentiobiose-glucose (T2) (saffron A) does not exhibit any neuroprotective activity; the relationship between the thickness of the outer nuclear layer of the retina and the thickness of the entire retina is, in fact, comparable to that of retinas of animals subjected to light damage without any treatment (diseased retinas).

Conversely, the value of the ratio between the thickness of the outer nuclear layer of the retina and the thickness of the entire retina, in animals treated with saffron of the invention, having a content of trans-crocin-4-gentiobiose-gentiobiose equal to or greater than 16.9% and of trans-crocin-3-gentiobiose-glucose equal to or greater than 8% (saffron B) is comparable to that of healthy animals (healthy retina).

These data demonstrate the neuroprotective activity of the saffron comprising trans-crocin-4-gentiobiose-gentiobiose in amounts equal to or greater than 16.9% and trans-crocin-3-gentiobiose-glucose equal to or greater than at or above 8%.

Example 4

Morphological Analysis of the Retina

The efficacy profile associated with the administration of a combination of saffron and curcumin according to the present invention in the activity of neuroprotection was verified by conducting a morphological analysis of the retina in SD albino rats subjected to light damage in a model of retinal degeneration, to quantify the damage and assess the possible protective activity of this combination of saffron and curcumin compared to that of saffron alone and curcumin alone.

The animals were divided into five groups:

Group 1: rats treated with saffron having a content of trans-crocin-4-gentiobiose-gentiobiose (T1) equal to or greater than 16.9% and of trans-crocin-3-gentiobiose-glucose (T2) equal to or greater than 8% (saffron);

Group 2: rats treated with the combination of saffron having a content of trans-crocin-4-gentiobiose-gentiobiose (T1) equal to or greater than 16.9% and of trans-crocin-3-gentiobiose-glucose (T2) equal to or greater than 8% and curcumin (curcumin+saffron);

Group 3: rats treated with curcumin alone (curcumin);

Group 4: rats untreated, but subjected to light damage (control-LD);

Group 5: healthy animals (control).

Group 1 animals were treated for 7 days with saffron dissolved in ordinary tap water, at a dose of 1 mg of saffron per kg of animal body weight. The treatment was prepared daily.

Group 2 animals were treated for 7 days with a combination comprising saffron and curcumin, at a dose of 1 mg of saffron and 5 mg of curcumin per kg of animal body weight.

Group 3 animals were treated for 7 days with curcumin, at a dose of 5 mg of curcumin, dissolved in oil, per kg of animal body weight.

On the seventh day the animals of groups 1, 2 and 3 were subjected to a light damage for 24 hours, and then were treated for another 7 days.

On the seventh day, group 4 animals were subjected to damage from light for 24 hours.

The animals of group 5 have not been subjected to the treatment or saffron based, curcumin or combination thereof, nor to light damage.

On the fourteenth day all animals were sacrificed, eyes explanted and retinas isolated.

The thickness of the outer nuclear layer of the retina (ONL), which contains the photoreceptors, and the thickness of the entire retina in the area of maximum damage of the retina backbone (defined as hot-spots) were then measured, and the ratio of these values was calculated.

The graph in FIG. 3 shows the values of these ratios.

The results demonstrate that the composition comprising the combination of saffron and curcumin according to the present invention is capable of exerting a greater activity than a composition containing the saffron alone or the curcumin alone, thus demonstrating a synergistic effect given by the combination of saffron and curcumin.

Figure 1:
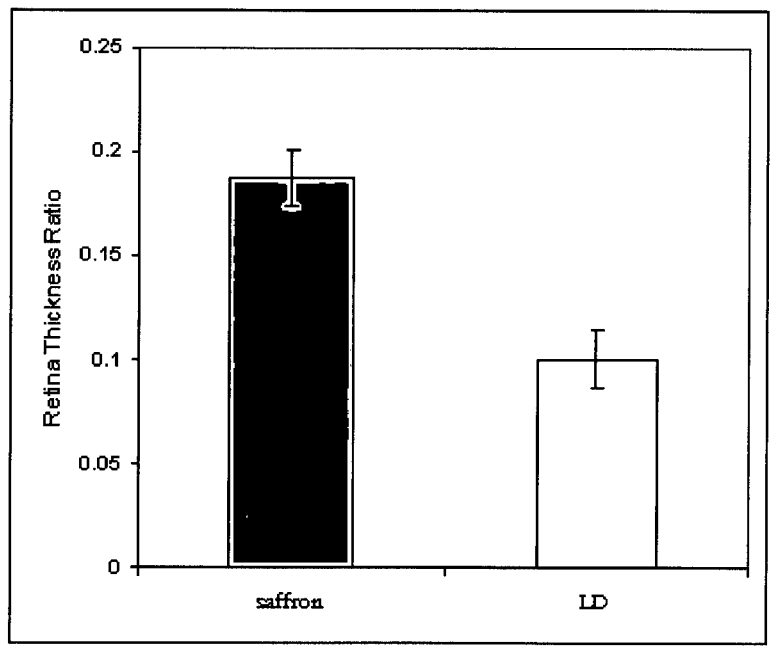
FIG. 1.
Representation of the ratio between the thickness of the outer nuclear layer of the retina (ONL) and the thickness of the entire retina, in a model of photoreceptors degeneration. In the figure are compared: animals treated with saffron and control animals (no treatment).
Figure 2:
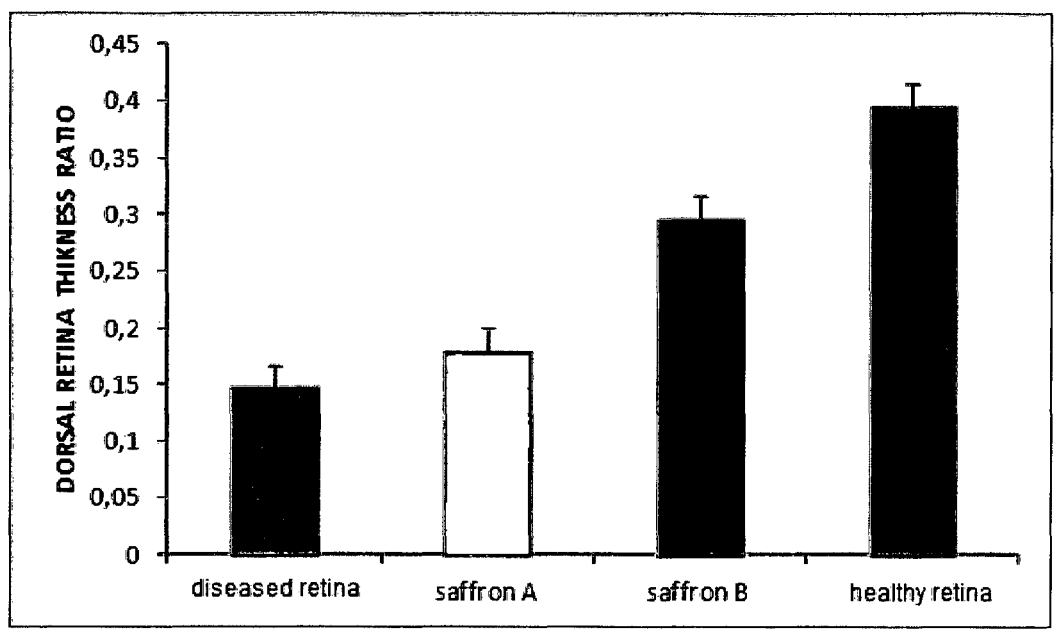
FIG. 2.
Representation of the ratio between the thickness of the outer nuclear layer of the retina (ONL) and the thickness of the entire retina, in a model of photoreceptors degeneration. In the figure are compared: animals treated with saffron comprising trans-crocin-4-gentiobiose-gentiobiose in an amount equal to or higher than 16.9% and trans-crocin-3-gentiobiose-glucose in an amount equal to or greater than 8% (saffron B); animals treated with saffron having a content of trans-crocin-4-gentiobiose-gentiobiose (T1) equal to 12% and trans-crocin-3-gentiobiose-glucose (T2) equal to 6% (saffron A); animals untreated, but subjected to light damage (diseased retina); and healthy animals (healthy retina).
Figure 3:
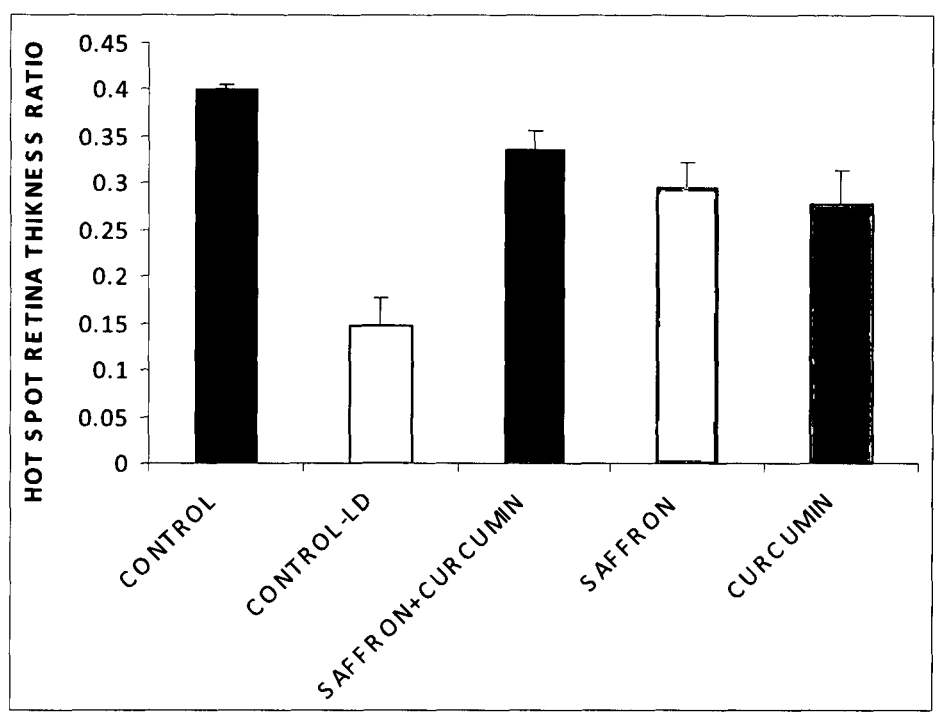
FIG. 3.
Representation of the ratio between the thickness of the outer nuclear layer of the retina (ONL) and the thickness of the entire retina, in a model of photoreceptors degeneration. In the figure are compared: animals treated with saffron having a content of trans-crocin-4-gentiobiose-gentiobiose (T1) equal to or greater than 16.9% and trans-crocin-3-gentiobiose-glucose (T2) equal to or greater than 8% (saffron); animals treated with the combination of saffron, having a content of trans-crocin-4-gentiobiose-gentiobiose (T1) equal to or greater than 16.9% and trans-crocin-3-gentiobiose-glucose (T2) equal to or greater than 8%, and turmeric (curcumin+saffron); animals treated with curcumin alone (curcumin); animals untreated, but subjected to light damage (control-LD); healthy animals (control).

The invention claimed is:

1. A method of treating a retinal degenerative eye disorder in a mammal, comprising administering to the mammal a pharmaceutical, dietary and/or food composition, wherein the composition comprises an effective amount of saffron, wherein the saffron includes trans-crocin-4-gentiobiose-gentiobiose in an amount equal to or greater than 16.9% by weight, based on a total weight of the saffron, and wherein the saffron includes trans-crocin-3-gentiobiose-glucose in an amount equal to or greater than 8% by weight, based on the total weight of the saffron.

2. The method of claim 1 wherein the retinal degenerative eye disorder is a hereditary retinal degeneration disorder or an induced retinal degeneration disorder.

3. The method of claim 2 wherein the hereditary retinal degeneration disorder is retinitis pigmentosa or Stargardt disease and the induced retinal degeneration disorder is an age related macular degeneration disorder.

4. The method of claim 1 wherein the saffron of the composition is a dried product obtained from an amount of *Crocus sativus* ranging between 5 mg and 50 mg.

5. The method of claim 1 comprising administering to the mammal the composition such that the patient receives the saffron in a daily dose of 20 mg/day.

6. The method of claim 1 wherein the composition further comprises an effective amount of curcumin.

7. The method of claim 6 wherein the curcumin of the composition is a dried product obtained from an amount of *Curcuma longa* ranging between 30 mg and 200 mg, and the saffron of the composition is a dried product obtained from an amount of *Crocus sativus* ranging between 5 mg and 50 mg.

8. The method of claim 6 comprising administering to the mammal the composition such that the patient receives the saffron in a daily dose of 20 mg/day and the curcumin in a daily dose of 100 mg/day.

9. The method of claim 1 wherein the mammal is a human.

10. The method of claim 1 wherein the composition comprises at least one physiological acceptable excipient.

11. The method of claim 1 wherein the composition is a tablet, a granulate, a dragee or a capsule.

12. The method of claim 1 wherein the saffron originates from Abruzzo, Umbria or Tuscany regions of Italy.

* * * * *